(12) United States Patent
Rossi et al.

(10) Patent No.: US 6,562,570 B1
(45) Date of Patent: May 13, 2003

(54) METHOD FOR IDENTIFYING ACCESSIBLE BINDING SITES ON RNA

(75) Inventors: John J. Rossi, Rancho Cucamonga, CA (US); Michaela Scherr, Oberusel (DE); Arthur D. Riggs, La Verne, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/536,393

(22) Filed: Mar. 28, 2000

Related U.S. Application Data

(60) Provisional application No. 60/127,529, filed on Apr. 2, 1999.

(51) Int. Cl.[7] .............................. C12Q 1/68; C12P 19/34
(52) U.S. Cl. ......................... 435/6; 435/91.1; 435/91.2
(58) Field of Search ........................... 435/6, 91.1, 91.2

(56) References Cited

U.S. PATENT DOCUMENTS 5,496,698 A * 3/1996 Draper et al. .................. 435/6
5,525,468 A * 6/1996 McSwiggen .................... 435/6

OTHER PUBLICATIONS

Albuquerque–Silva et al., "Tailing cDNAs with terminal deoxynucleotidyl transferase in RT–PCR assays to identify ribozyme cleavage products," *Nucleic Acids Research*, 1998, vol. 26, No. 13, pp. 3314–3316.

Bertrand et al., "Facilitation of hammerhead ribozyme catalysis by the nucelocapsid protein of HIV–1 and the heterogeneous nuclear ribonucleoprotein A1," *The EMBO Journal*, vol. 13, No. 12, pp. 2904–2912, 1994.

Chen et al., "In vivo, high–resolution analysis of yeast and mammalian RNA–protein interactions, RNA structure, RNA splicing and ribozyme cleavage by use of terminal transferase–dependent PCR," *Nucleic Acids Research*, 2000, vol. 28, No. 7, pp. 1656–1664.

Scherr et al., Nucleic Acids Res. 26(22), 5079–5085 (1998).*

Monia, B. P., et al., (1996), "Antitumor activity of a phosphorothioate antisense oligodeoxynucleotide targeted against C–raf kinase," *Nature Med.*, vol. 2, 668–675.

Campbell, T. B., et al., (1997), "The effect of structure in a long target RNA on ribozyme cleavage efficiency," *Nucleic Acids Res.*, vol. 25, 4985–4993.

Dreyfuss, G., et al., (1993), "hnRNP Proteins and the Biogenesis of mRNA," *Annu. Rev. Biochem.*, vol. 62, 289–321.

Ho, S. P., et al., (1996), "Potent antisense oligonucleotides to the human multidrug resistance–1 mRNA are rationally selected by mapping RNA–accessible sites with oligonucleotide libraries," *Nucleic Acids Res.*, vol. 24, 1901–1907.

Milner, N., et al., (1997), "Selecting effective antisense reagents on combinatorial oligonucleotide arrays," *Nature Biotechnol.*, vol. 15, 537–541.

Birikh, K. R., et al.,(1997), "Probing accessible sites for ribozymes on human acetylcholinesterase RNA," *RNA*, vol. 3, 429–437.

Lima, W. F., et al., (1997), "Combinatorial Screening and Rational Optimization for Hybridization to Folded Hepatitis C Virus RNA of Oligonucleotides with Biological Antisense Activity," *J. Biol. Chem.*, vol. 272, 626–638.

Ho, S. P., et al., (1998), "Mapping of RNA accessible sites for antisense experiments with oligonucleotide libraries," *Nature Biotechnol.*, vol. 16, 59–63.

Campbell, T. B. et al., (1995), "Identification of ribozymes within a ribozyme library that efficiently cleave a long substrate RNA," *RNA*, vol. 1, 598–609.

Lieber, A., et al., (1995), "Selection of efficient cleavage sites in target RNAs by using a ribozyme expression library," *Mol. Cell. Biol.*, vol. 15, 540–551.

Vaish, N. K., et al., (1997), "Isolation of hammerhead ribozymes with altered core sequences by in vitro selection," *Biochemistry*, vol. 36, 6495–6501.

Komura, J., et al., (1998), "Terminal transferase–dependent PCR: a versatile and sensitive method for in vivo footprinting and detection of DNA adducts," *Nucleic Acids Res*, 26(7):1807–11.

Anzick, S. L., et al., (1997), "AIB1, a steriod receptor coactivator amplified in breast and ovarian cancer," *Science*, 277(5328): 965–8.

* cited by examiner

*Primary Examiner*—Kenneth R. Horlick
(74) *Attorney, Agent, or Firm*—Rothwell, Figg, Ernst & Manbeck

(57) ABSTRACT

A method for identifying sites on a target RNA which are accessible to pairing by antisense DNA, ribozymes or DNAzymes. Native or in vitro-synthesized target RNA is incubated with defined ODNs and RNase H, or with a random or semi-random ODN library and RNase H, or with defined ribozymes or DNAzymes, or with a semi-random ribozyme or DNAzyme library, in a cell extract containing endogenous RNA-binding proteins, or in a medium which mimics a cell extract due to presence of one or more RNA-binding proteins. Any antisense ODN, ribozyme or DNAzyme which is complementary to an accessisble site in the target RNA hybridizes to that site and the RNA is cleaved at that site. Reverse transcription can be used to generate a first strand DNA from the RNA cleavage product, and terminal deoxynucleotidyl transferase-dependent polymerase chain reaction (TDPCR) can be used to identify sites on target RNA to which antisense ODNs, ribozymes or DNAzymes have bound and cleavage has occurred.

18 Claims, 2 Drawing Sheets

METHOD FOR IDENTIFYING ACCESSIBLE BINDING SITES ON RNA

CROSS REFERENCE TO RELATED APPLICATION

This application claims the benefit of provisional application Serial No. 60/127,529, filed Apr. 2, 1999.

GOVERNMENT RIGHTS

This invention was made under grants AI29329, AI142552 and GM50575 from the United States National Institutes of Health. The United States government has certain rights in the invention.

BACKGROUND

Worldwide efforts to determine the complete nucleotide sequence of the human genome as well as the genomes of other organisms will result in a huge catalog of sequence information. The goals of the human genome program are to have the project completed by early in the first decade of the 21st century. A major challenge which follows is to identify the functions of the tens of thousands of open reading frames that will result.

One of the technologies which will be utilized for this is antisense-, ribozyme- or DNAzyme-mediated destruction of the sequences, followed by phenotypic and more detailed physiologic and biochemical analyses of cells in which the target has been destroyed. A major problem confronting all antisense technologies is that of rapid throughput screening of sites accessible to pairing by the antisense DNAs and RNAs.

Several approaches have been described to determine the accessibility of a target RNA molecule to antisense or ribozyme inhibitors. One approach uses an in vitro screening assay applying as many antisense oligodeoxynucleotides (antisense ODNs) as possible. Monia et al., *Nature Med.* 2:668–675 (1996); Milner et al., *Nature Biotechnol.* 15:537–541 (1997). Another utilizes random libraries of ODNs. Ho et al., *Nucleic Acids Res.* 24:1901–1907 (1996) (Ho et al. I); Birikh et al., *RNA* 3:429–437 (1997); Lima et al., *J. Biol. Chem.* 272:626–638 (1997). The accessible sites can be monitored by RNase H cleavage. Birikh et al, supra; Ho et al., Nature Biotechnol. 16:59–63 (1998) (Ho et al., II). RNase H catalyzes the hydrolytic cleavage of the phosphodiester backbone of the RNA strand of a DNA-RNA duplex.

A pool of semi-random, chimeric chemically synthesized ODNs have been used to identify accessible sites cleaved by RNase H on an in vitro synthesized RNA target. Primer extension analyses were used to identify these sites in the target molecule. Lima et al., supra. Other approaches for designing antisense targets in RNA are based upon computer assisted folding models for RNA. Several reports have been published on the use of random ribozyme libraries to screen effective cleavage. Campbell et al., *RNA* 1:598–609 (1995); Lieber et al., *Mol. Cell Biol.* 15, 540–551 (1995); Vaish et al., *Biochemistry* 36:6459–6501 (1997).

In vitro approaches which utilize random or semi-random libraries of ODNs and RNase H seem to be more useful than computer simulations. Lima et al., supra. However, use of in vitro synthesized RNA does not provide satisfactory results for predicting the accessibility of antisense ODNs in vivo. Recent observations suggest that annealing interactions of polynucleotides are influenced by RNA-binding proteins. Tsuchihashi et al., *Science* 267:99–102 (1993); Portman et al., *EMBO J.* 13:213–221 (1994); Bertrand and Rossi, *EMBO J.* 13:2904–2912 (1994). It is therefore important to utilize cellular RNA-binding proteins in assays for elucidating RNA target accessibility to antisense, ribozyme or DNAzyme binding.

SUMMARY OF THE INVENTION

Our invention provides a method for identifying sites on target endogenous cellular (native) RNAs or in vitro-synthesized RNAs which are accessible to antisense, ribozyme, or DNAzyme binding. The underlying principles are that accurate predictions of the folded state of RNA within a cell are not possible, and that binding of antisense ODNs, ribozymes or DNAzymes to a substrate RNA under physiological conditions can be used to identify sites for antisense-mediated, ribozyme-mediated or DNAzyme-mediated RNA destruction or inhibition.

In our method we incubate native or in vitro-synthesized RNAs with defined antisense ODNs, ribozymes or DNAzymes, or with a random or semi-random ODN, ribozyme or DNAzyme library, under hybridization conditions in a reaction medium which is a cell extract containing endogenous RNA-binding proteins, or which mimics a cell extract due to presence of one or more RNA-binding proteins. Any antisense ODN, ribozyme or DNAzyme which is complementary to an accessible site in the target RNA will hybridize to that site. When defined ODNs or an ODN library is used, RNase H is present during hybridization or is added after hybridization to cleave the RNA where hybridization has occurred. RNase H can be present when ribozymes or DNAzymes are used, but is not required, since the ribozymes and DNAzymes cleave RNA where hybridization has occurred. In a preferred embodiment, we use a random or semi-random ODN library in cell extracts containing endogenous mRNA, RNA-binding proteins and RNase H. Examples of our invention using defined antisense ODNs to target native MRNA in cell extracts are reported in Scherr and Rossi, *Nucleic Acids Res.* 26(22):5079–5085 (1999) and included as Example 2 below.

Various methods can be used to identify sites on target RNA to which antisense ODNs, ribozymes or DNAzymes have bound and cleavage has occurred. We prefer to use terminal deoxynucleotidyl transferase-dependent polymerase chain reaction (TDPCR) for this purpose. TDPCR is described in Komura and Riggs, *Nucleic Acids Res.* 26(7): 1807–11(1998). In order to take full advantage of TDPCR, we incorporate a reverse transcription step to convert the RNA template to DNA, followed by TDPCR. In our invention, the 3' termini needed for the TDPCR method are created by reverse transcribing the target RNA of interest with any suitable RNA dependent DNA polymerase (reverse transcriptase). We do this by hybridizing a first ODN primer (P1) to the RNA in a region which is downstream (i.e., in the 5'→3' direction on the RNA molecule) from the portion of the target RNA molecule which is under study. The polymerase in the presence of dNTPs copies the RNA into DNA from the 3' end of P1 and terminates copying at the site of cleavage created by either an antisense ODN/RNase H, a ribozyme or a DNAzyme. The new DNA molecule (referred to as the first strand DNA) serves as first template for the PCR portion of the TDPCR method.

We then carry out the TDPCR procedure, which involves the following steps. We react the reverse-transcribed DNA with guanosine triphosphate (rGTP) in presence of terminal deoxynucleotidyl transferase (TdT) to add an $(rG)_{2-4}$ tail on the 3' termini of the DNA molecules. We then ligate a double-stranded ODN linker having a 3' $C_{2-4}$ overhang on one strand which base-pairs with the $(rG)_{2-4}$ tail. We then add two PCR primers. One primer we call a linker primer (LP) because it is complementary to the strand of the TDPCR linker which is ligated to the $(rG)_{2-4}$ tail (sometimes referred to as the lower strand) The other primer (P2) can be the same as P1, but preferably it is nested with respect to P1, i.e., it is complementary to the target RNA in a region which is at least partially upstream (i.e. in the 3'→5' direction on the RNA molecule) from the region which is bound by P1, but it is downstream of the portion of the target RNA molecule which is under study. (In other words, the portion of the target RNA molecule which is under study to determine whether it has accessible binding sites is that portion which is upstream of the region that is complementary to P2.) We then carry out PCR in the known manner in presence of a DNA polymerase and dNTPs to amplify DNA segments defined by primers LP and P2.

The amplified product can be captured by any of various known methods and subsequently sequenced on an automated DNA sequencer, providing precise identification of the cleavage site. Once this identity has been determined, defined sequence antisense DNA, ribozymes or DNAzymes can be synthesized for use in vitro or in vivo.

Our invention includes the use of reverse transcription followed by TDPCR to identify sites to which antisense ODNs, ribozymes or DNAzymes have bound, regardless of whether the hybridization/cleavage reactions were carried out in a medium which is a cell extract or which mimics a cell extract.

DETAILED DESCRIPTION OF THE INVENTION

Antisense ODNs, Ribozymes and DNAzymes

Figure 1:
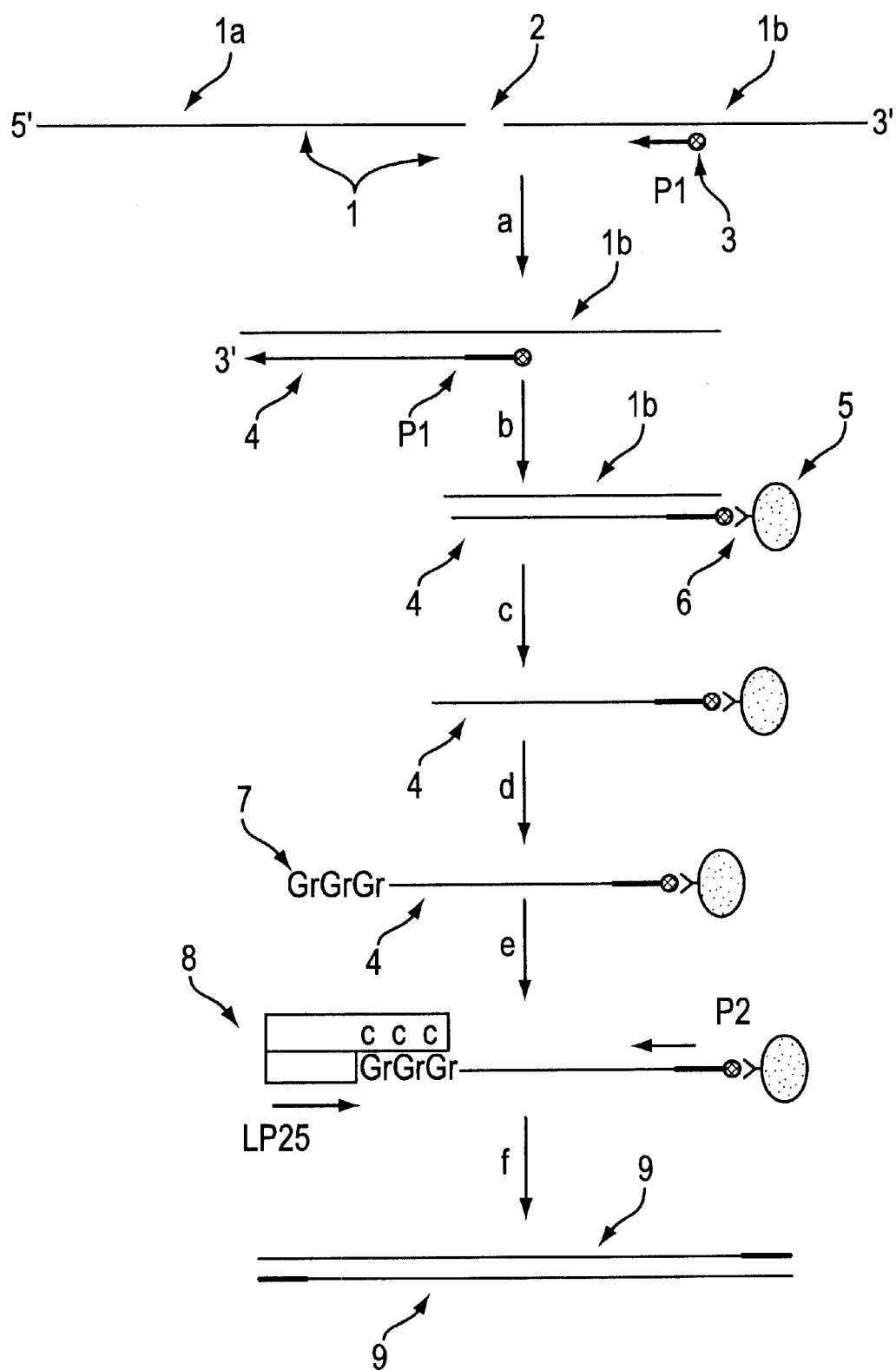
FIG. 1 is a diagram of the reverse transcription-TDPCR (RT-TDPCR) methodology used in our invention.

Random and semi-random ODN libraries which can be used in our invention include the random decadeoxyribonucleotide ($dN_{10}$) libraries of Birikh et al. and Lima et al., supra, and the semi-random libraries of Ho et al. (I) and (II), supra:

5' mmmGNNNmmmm 3'

5' mmmANNNmmmm 3'

5' mmmCNNNmmmm 3'

5' mmmTNNNmmmm 3' where m G, A, C and T are 2'-deoxyribonucleotides, m and N denote a random mixture of 2'-methoxyribonucleotides and 2'-deoxyribonucleotides, respectively.

Although libraries of ODNs having only 4 to 8 contiguous 2'-deoxyribonucleotides can be used, it is preferable for the ODNs to have at least 9 contiguous 2'-deoxyribonucleotides. The reason is that mammalian RNase H cleaves RNA most efficiently if there are at least 9 contiguous base pairs of RNA/DNA hybrid. In the optimal embodiment of this invention, the antisense ODNS comprise 9 to 11 contiguous 2'-deoxyribonucleotides. Antisense ODNs with more than 11 contiguous 2'-deoxyribonucleotides could be used, but obviously, more 2'-deoxyribonucleotides result in larger degenerate pools. Thus, as a practical matter, the number of 2'-deoxyribonucleotides should not exceed about 12–15.

The contiguous 2'-deoxyribonucleotide sequence can be flanked by 2'-methoxyribonucleotide sequences to prevent the ends of the antisense ODNs from serving as substrates for RNase H. The flanking 2'-methoxyribonucleotide sequences will not serve as a substrate for RNase H. Only the 2'-deoxyribonucleotide core sequences provide a backbone which can be functionally recognized by the RNase H. Although we have used antisense ODNs with flanking 2'-methoxyribonucleotide sequences in our experiments, the flanking sequences are not required, and it may be preferable to omit them, to minimize the size of the degenerate pools.

The semi-random ribozyme libraries which can be used in our invention are mixtures of hammerhead or hairpin ribozymes. Hammerhead ribozymes comprise a defined catalytic oligoribonucleotide-containing core with randomized or semi-randomized RNA-binding flanking sequences. The RNA-binding flanking sequences can be ribonucleotide or 2'-deoxyribonucleotide sequences. The flanking sequences are generally about 6 to 15 nucleotides in length. Examples of hammerhead ribozyme catalytic cores include:

5' CUGAUGA-Y-GAAA 3' where Y is a ribonucleotide sequence (e.g., 5' GUCCGUGAGGAC 3') (Seq ID 15) that base pairs in the manner required for catalytic cleavage of substrate RNA,, and A, U, G and C are all ribonucleotides, as disclosed in Rossi U.S. Pat. No. 5,695,938;

5' CUGAUGA-Y-GAAA 3' where A, U, G and C are ribonucleotides, and Y is a 2'deoxynucleotide sequence (e.g. d(GAGGAGTGCCTC)) (Seq ID 16) that base pairs in the manner required for catalytic cleavage of substrate RNA by the deoxyribonucleotide sequences, as disclosed in Rossi et al. U.S. Pat. No. 5,149,796; and 5' CUGAUGGUCCGUAGGACGAAAC 3' Seq ID 17 where A, U, G and C are ribonucleotides, as disclosed in Lieber et al., supra.

An example of a hairpin ribozyme library which can be used in our invention is:

5' NNNNNNNAGAANNNN-Z 3' where N is any nucleotide and Z is a sequence that base pairs to form a hairpin as required for catalytic cleavage of substrate RNA, e.g., 5' ACCAGGAAACCACGUUGUAUAUUACCUGGU 3' (Seq ID 21).

The semi-random DNAzyme libraries which can be used in our invention are mixtures of DNAzymes which comprise a defined catalytic oligodeoxyribonucleotide core with randomized or semi-randomized 2'-deoxyribonucleotide flanking sequences. The flanking sequences are generally about 6 to 15 nucleotides in length. Examples of DNAzyme catalytic cores include:

```
5' TCCGAGCCGGACGA 3'      Seq ID 18

5' AGGCTAGCTACAACGA 3'    Seq ID 19, and

5' GGGCTAGCTACAACGA 3'    Seq ID 20
``` where A, G, T and C are all 2'-deoxyribonucleotides, as disclosed in Santoro and Joyce, *Proc. Natl. Acad. Sci. US,* 94:4262–4265 (1997).

Defined antisense ODNs, ribozymes and DNAzymes for use in our invention can be designed based on known sequence information and computer assisted folding models for RNA for identification of potential binding sites. Patzel et al., *Nature Biotechnol.* 16:64–68 (1988); Sczakiel et al., *Antisense Res. Dev.* 3:45–52 (1993). As in the case of random or semi-random ODN libraries, defined ODNs comprise 4 to about 15, preferably about 9 to about 11, contiguous 2'-deoxyribonucleotides, optionally with flanking sequences of 2'-methoxyribonucleotides. Defined ribozymes and DNAzymes comprise the same catalytic portions as the molecules in the ribozyme and DNAzyme libraries, but with defined-sequence RNA-binding portions.

The defined antisense ODNs, ribozymes and DNAzymes, and the random and semi-random ODN, ribozyme and DNAzyme libraries can all be made by standard nucleoside phosphoramidite, phosphotriester or phosphonate chemistry, on commercially available instruments, using methods known to those skilled in the art of DNA/RNA synthesis.

Hybridization/Cleavage Reaction Medium

In one embodiment of our invention, defined antisense ODNs, ribozymes or DNAzymes, or a random or semi-random library of ODNs ribozymes or DNAzymes are incubated with target RNA in a medium which is a cell extract containing endogenous target RNA, endogenous RNase H, and endogenous RNA binding proteins. Cell extracts that are rich in RNA-binding proteins and RNAse H activity and contain endogenous RNAs can be prepared as described in Scherr and Rossi, supra. This method was originally designed as a source of endogenous RNA polymerase III, and for this reason we refer to cell extracts made by this method as polymerase III extracts. Other Dounce homogenization methods followed by low speed centrifugation can be used to prepare cell extracts that are rich in RNA-binding proteins and RNAse H activity and contain endogenous RNAs.

In the work reported in Scherr and Rossi, supra, we used NIH 3T3 cells as a source of polymerase III extract, and the extract was used with defined ODNs to identify binding sites on murine DNA methyl transferase (MTase). The method of this invention, can be used with NIH 3T3 polymerase III extracts to identify accessible sites in other endogenous RNAs in the extract.

Other cells can be used as a source of endogenous target RNA. For example, in the experiments reported below, we use a breast cancer cell line MCF-7 to prepare an extract rich in AIB1 mRNA. AIB1 is a gene which is amplified in many breast cancers. Various cancer cell lines can be used as a rich source of mRNAs and heterogeneous nuclear RNAs (hnRNAs), including pre-mRNAs, produced by genes which are amplified in those lines. Any cell line which expresses the RNA of interest, regardless of whether it is expressed at basal levels or is amplified in expression can be a source of RNAs for this method. Other examples of cell sources are virally infected cells such as HIV-1, cell lines expressing mRNAs which are targets for inactivation because of basic studies or for potential therapeutic targeting. All organisms have RNaseH, and therefore extracts harboring endogenous messages and RNaseH can be used with this invention. For preparation of extracts, this procedure is not limited to mammalian cells, but can be utilized with bacterial, yeast, fungal, insect and plant cells.

Alternatively, in vitro-synthesized target RNA can be added to a cell extract rich in RNA-binding proteins and RNase H activity to provide a suitable medium. Our invention can be used to determine accessible binding sites in any RNA, including MRNA, hnRNA, transfer RNA (tRNA), ribosomal RNA (rRNA), and small nuclear RNA (snRNA).

In another embodiment of our invention, in vitro-synthesized target RNA can be added to a medium which mimics a cell extract, i.e., which causes the RNA to fold into a conformation approximating its conformation in a natural intracellular milieu that is rich in RNA binding proteins. A medium which mimics a cell extract can be prepared by incorporating one or more RNA-binding proteins selected from the group consisting of heterogeneous nuclear RNA-binding proteins (hnRNPs) and mRNA-binding proteins (mRNPs) into an aqueous solution that contains magnesium chloride and potassium chloride in proper concentration to simulate physiological conditions, e.g., 2 mM $MgCl_2$, 150 mM KCl, pH 7.5. For a review of mRNPs, see Dreyfuss et al., *Annu. Rev. Cell Biol.,* 2:459–498 (1986). For a review of hnRNPs, see Dreyfuss et al., *Annu. Rev. Biochem.* 62:289–321 (1989). Optimally, the medium contains heterogeneous nuclear riboprotein A1 (hnRNP A1), which has been shown to facilitate hammerhead ribozyme catalysis. Bertrand and Rossi, supra.

Conditions for hybridization of defined ODNs and ODN pools are described in Sambrook et al., *Molecular Cloning, a Laboratory Manual,* Second Edition, Vol. 2, pages 11.45–11.57, Cold Spring Harbor Laboratory Press (1989). The same conditions apply to hybridization of ribozymes and DNAzymes.

At the end of the hybridization/cleavage reaction, the reaction mixture can be treated with DNase I to destroy the ODNs and any other DNA present, as disclosed in Scherr and Rossi, supra. However, this is not essential, as shown by the Example below, in which the hybridization reaction was stopped by adding phenol followed by ethanol precipitation. The ODNs are dissolved in the ethanol and so removed when starting the following reverse transcription reaction.

RT-TDPCR

FIG. 1 depicts a preferred method of carrying out TDPCR. A target RNA molecule 1 has been cleaved at 2 by an antisense ODN and RNase H, or by a ribozyme or DNAzyme included within a random or semi-random library to produce two fragments 1a and 1b. ODN Primer P1 labeled at its 5' end with biotin 3 is bound to the RNA molecule in a region which is downstream (i.e., in the 5'→3' direction on the RNA molecule) from the site of cleavage. In step a primer P1 is extended by reverse transcription to the point of cleavage 2, producing a DNA molecule 4 (sometimes referred to as the 1st strand DNA) hybridized to RNA molecule 1b. In step b magnetic beads 5 coated with streptavidin 6 are added. The streptavidin binds to the biotin, and a magnet is used to separate the DNA/RNA from the reaction mixture. In step c the hybrid is treated with NaOH to melt away the RNA, producing a single-stranded DNA molecule 4 with a 3' terminus needed for TDPCR.

In step d, the 3' end of the first strand DNA 4 is tailed with 2 to 3 riboguanosine moieties rG 7 using terminal deoxynucleotidyl transferase and rGTP. In step e, these rGs are annealed to a linker 8 which has 3'-deoxycytosines C which base pair with the riboguanosines. The linker is ligated to the first strand DNA 4. Amplification primers LP and P2 are added. In step f, the upper strand of the linker acts as primer and is extended to the 5' end of the first strand DNA 4 to produce a double-stranded DNA molecule. Standard PCR is carried out on this double-stranded DNA molecule using primers P2 and LP to provide the PCR products 9.

Primer P1 can be labeled with any member of a specific-binding pair, and the first strand DNA can be separated by affinity separation using the other member of the specific-binding pair immobilized on any solid support. It is not essential that P1 be labeled. When an unlabeled P1 is used, the RNA/DNA hybrid resulting from reverse transcription is first treated with heat or NaOH to melt away the RNA, then the TDPCR procedure can be carried out.

Other Identification Methods

Although we prefer to use reverse transcription followed by TDPCR, other methods can be used to identify sites on target RNA to which antisense ODNs, ribozymes or DNAzymes have bound. For example, reverse transcription followed by blunt-ended ligation can be used, and amplification methods other than PCR can be used, such as strand displacement amplification as disclosed in U.S. Pat. No. 5,648,211. An in vitro transcribed PCR can be labeled with $^{32}P$ dUTP, and the cleavage product or products detected without amplification, as described in Scherr and Rossi, supra.

Sequencing

The amplified product can be captured and subsequently sequenced on an automated DNA sequencer, providing precise identification of the cleavage site. Once this identity has been determined, defined sequence oligo DNAs, ribozymes or DNAzymes can be synthesized for use in vivo or in vitro. Various methods known to those skilled in the art can be used to capture the amplified product. One method, illustrated in the Example below, is to sperate the amplified product on an agarose or polyacrylamide gel. Another method is to label the primer P2 or LP with one member of a specific binding pair and affinity purify the amplification products using the other member of the binding pair immobilized on a solid support. Another method is to hybridize to one strand of the amplified DNA a complementary probe which is labeled with one member of a specific binding pair and affinity purify using the other member of the binding pair immobilized on a solid support.

EXAMPLE 1

This an example of site mapping using AIB1 mRNA (Anzick et al., Science 277:965–967 (1997), GenBank accession number AFO12108). In the sequence listings, all linkages are phosphodiester linkages unless otherwise stated.

The nucleotide sequences listed below were prepared using standard phosphoramidite synthesis chemistry on a commercial DNA/RNA synthesizer.

Random ODN Libraries

Semi-random oligonucleotide libraries consisting of two pools of oligonucleotides of the following composition:

```
Pool 1    5' N*N*N*N*N* NNN AGN NNN N*N*N*N*N* 3'

Pool 2    5' N*N*N*N*N* NNN ACN NNN N*N*N*N*N* 3'
```

The N*'s represent 2'-methoxyribonucleotide moieties A, G, C or T in random sequence. The N's represent 2'-deoxyribonucleotide moieties A, G, C or T in random sequence. The fixed 2'-deoxyribonucleotides A and C or G in the center of the ODN's were chosen to direct these pools to potential hammerhead ribozyme cleavage sites. For instance, pool 1 would pair with sequences containing a CUN, and pool 2 with sequences containing a GUN. Since the hammerhead specificity is NUN, where N=any ribonucleotide, we have only covered ½ of the potential sites with these two pools. Additional pools containing NAT and NAA, which would identify AUN and UUN, could easily be made as well.

Defined ODNs

The numbers in parentheses following the sequence ID numbers are the complementary NTs of AIB1 mRNA

```
Non-sense  5' CCGTATCGCTCGGGTTAAGC 3' Seq ID 1

AIB#123    5' TATTGGTCTCTGAGTCCACC 3' Seq ID 2
                                         (123–142)

AIB#276    5' CTGCAGGTAAGACCTTGTCC 3' Seq ID 3
                                         (276–295)

AIB#298    5' CTCCCGTCTCCGTTTTTCAC 3' Seq ID 4
                                         (298–317)

AIB#314    5' TATATTTACTTTCCTGCTCC 3' Seq ID 5
                                         (314–333)
```

The two residues at the 3' ends of the defined ODNs had phosphorothioate linkages.

```
                     Primers
AIB  5' catccaatgcctgaagtaaa 3'                Seq ID 6
#1                                              (548–67)
AIB  5' cctgaagtaaaagcggtcctaagg 3'             Seq ID 7
#2                                              (535–58)
AIB  5' gcggtcctaaggagtctttatcaataactc 3'       Seq ID 8
#3                                              (517–46)
A#1  5' ctctggcgaatttcaggac 3'                  Seq ID 9
                                                (841–59)
A#2  5' caggactggcgtttatgtcttc 3'               Seq ID 10
                                                (825–46)
A#3  5' gtcttccagaatatcatgtggtgttttc 3'         Seq ID 11
                                                (803–30)
```

AIB#1 and A#1, which correspond to P1 in FIG. 1, were labeled at the 5' end using biotin phosphoramidite. AIB#2 and A#2 correspond to P2 in FIG. 1. AIB#3 and A#3 were 5' end labeled with $^{32}P$, as described below. The AIB# set of primers was used in one experiment, and the A# set was used in another experiment, as described below.

```
    TDPCR linker β and linker primer LP 25

β      5' gcggtgacccgggagatctgaattccc 3'   Seq. ID 12
       3' cgccactgggccctctagacttaa 5'      Seq. ID 13
LP-25  5' gcggtgacccgggagatctgaattc 3'     Seq. ID 14
```

Linker β was prepared by hybridizing Seq ID 12 and Seq ID 13 as described in Scherr and Rossi, supra.

Preparation of Cellular Extracts

The cell extracts used in these studies were prepared from MCF-7 cells, a breast cancer line. Approximately $8 \times 10^7$ cells were pelleted and washed twice in phosphate-buffered saline. The pellets were resuspended in twice the volume of the cell pellet of hypotonic swelling buffer (7 mM Tris-HCl, pH 7.5, 7 mM KCl, 1 mM $MgCl_2$, 1 mM [beta]-mercaptoethanol) and after 10 min incubation on ice, transferred to a Dounce homogenizer (VWR, San Diego, Calif.) followed by 20 strokes with a tight pestle B and addition of 1/10th of the final volume of neutralizing buffer (21 mM Tris-HCl, pH 7.5, 116 mM KCl, 3.6 mM MgCl$_2$, 6 mM [beta]-mercaptoethanol). The homogenate was centrifuged at 20,000×g for 10 min at 4° C. The supernatants, which are rich in RNA-binding proteins and RNase H activity and contain endogenous mRNAs, were transferred to an Eppendorf tube on ice and used immediately or stored at −70° C. in hypotonic buffer containing 45% glycerol.

Hybridization of Antisense ODNs and Cleavage of MRNA

The experiments were carried out in a total volume of 40 µl, containing 1 µl (40 units) RNase inhibitor (RNasin®, Promega), 1 µg semi-random oligodeoxynucleotide library or 50 nM defined ODN, and 38 µl polymerase III extract prepared from MCF-7 cells as described above. The library or defined ODN and extract were incubated for 10–20 min at 37° C. To stop the reaction the mixture was then extracted with phenol-chloroform followed by an ethanol precipitation in the presence of 1 µl of glycogen.

Reverse Transcription

One third of the reaction was utilized for a RT-TDPCR. The reverse transcription was performed by annealing the RNA (from the cell extract) to 1 pmol of biotinylated primer AIB#1 (Seq ID 6) or A#1 (Seq ID 9), in 1×RT-buffer, containing 10 mM Tris-HCl pH 8.3, 50 mM KCl, 10 mM MgCl$_2$, 6 units RNasin and 2.5 mM dNTPs in a total volume of 10 µl at 85° C. for 5 min. After cooling down to room temperature 10 µl of reverse transcriptase mix containing 10 mM Tris-HCl, pH 8.3, 50 mM KCl, 5 mM MgCl$_2$, 10 units RNasin and 70 units of Moloney murine leukemia virus reverse transcriptase (M-MLV-RT) (Bethesda Research Labs) was added to each sample. The reaction was performed at 42° C. for 1 h, then the the M-MLV RT was heat-inactivated at 95 for 5 min.

Tailing of 3' Terminus of DNA

Magnetic beads coated with streptavidin (Dynabeads® M-289, Dynal Corp.) were used to immobilize the biotinylated first strand DNA. The beads were washed with 2×binding buffer (2×BW) and resuspended in 2× vol of 2×BW. Each sample was added to the bead solution for 30 min. The supernatant was removed using a magnet and the beads treated with 50 µl of 0.15 M NaOH at 37° C. for 10 min. The supernatant was removed and the beads were washed again with another 50 µl of 0.15 M NaOH. After removing the supernatant, the beads were equilibrated by washing 3 times with 200 µl 10 mM Tris-HCl, pH 7.5, 1 mM EDTA (TE, pH 7.5). The beads were resuspended in 10 µl of TE, pH 7.5, and mixed with 10 µl of TdT consisting of 10 units of Tdt (BRL) and 4 nM rGTP in 2×TdT-buffer. The tailing was carried out at 37° C. for 15 min.

Ligation of TDPCR Linker

The rG-tailed DNA on the beads was washed 2× with 200 ml 10.5 µl TE, pH 7.5 for the ligation reaction. 10.5 µl of ligation solution containing 143 mM Tris-HCl, pH 7.5, 3 mM MgCl$_2$, 3 mM DTT, 3 mM rATP was added to 15 µl rG-tailed DNA. After addition of 3 µl TDPCR linker (20 µM; Seq ID 12 and 13) and T4-DNA ligase (Promega, 3 units/µl), the mixture of 30 µl was incubated at 17° C. overnight.

TDPCR

To the ligation reaction are added 40 µl of PCR mix consisting of 27.4 µl of water, 10 µl of 5×Taq-buffer (200 mM NaCl, 50 mM Tris-HCl, pH 8.9, 0.05% (w/v) gelatin, 0.1 µl of 1 M MgCl$_2$, 0.5 µl of 25 mM dNTP mix, 0.5 µl of 20 µM primer AIB#2 (Seq ID 7) or A#2 (Seq ID 10), 0.5 µM LP-25 (Seq ID 14) and 1 µl AmpliTaq (5 units/µl). PCR was performed as following: 45 sec at 95° C., 2 min at 57° C., and 3 min at 74° C. (25 cycles).

Labeling of Amplified DNA

Figure 2:
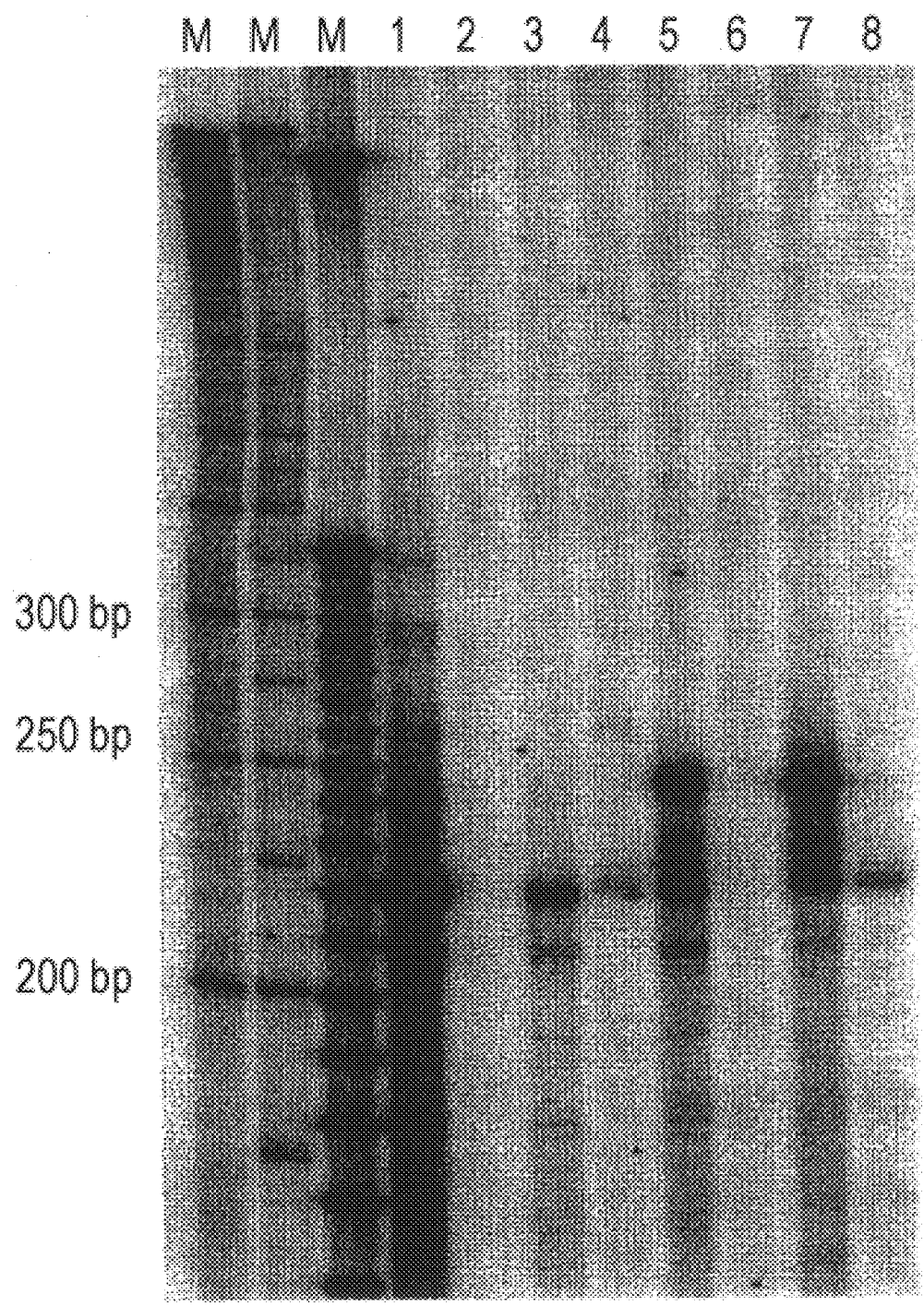
FIG. 2 is an autoradiograph showing the results of the Example below using the AIB#1 set of primers described below.

Direct labeling after PCR: Primers AIB#3 (Seq ID 8) and A#3 (Seq ID 11) were 5' end-labeled with $^{32}$P using $^{32}$P-γATP and T4 polynucleotide kinase (New England Biolabs) according to the instruction supplied by the manufacturer. 10 µl of the PCR-product was directly labeled by addition of 1 µl labeled primer 3 (AIB#3 or A#3). Labeling was done with a thermocycler (Perkin Elmer) for 6 cycles of 1 min at 95° C., 3 min at 59° C., and 2 min at 72° C. 5 µl of the labeled product was mixed with formamide and loaded directly onto an 8% denaturing sequencing gel along with $^{32}$P-labeled DNA ladder. The separated fragments were visualized by autoradiography or the use of a phosphorimager. The autoradiograph for the experiments using the AIB# set of primers is shown in FIG. 2. In FIG. 2:

Lanes M—molecular weight markers

Lane 1—RT-TDPCR product from MCF-7 cell extract treated with control ODN (Seq ID 1)

Lane 2—RT-TDPCR product from MCF-7 cell extract treated with AIB#123 (Seq ID 2)

Lane 3—RT-TDPCR product from MCF-7 cell extract treated with AIB#276 (Seq ID 3)

Lane 4—RT-TDPCR product from MCF-7 cell extract treated with AIB#298 (Seq ID 4)

Lane 5—RT-TDPCR product from MCF-7 cell extract treated with AIB#314(Seq ID 5)

Lane 6—RT-TDPCR product from MCF-7 cell extract treated with semi-random pool 1

Lane 7—RT-TDPCR product from MCF-7 cell extract treated with semi-random pool 2

Lane 8—RT-TDPCR product from MCF-7 cell extract treated with control ODN (Seq ID 1)

Only AIB#298 (band is not visible in this exposure, but is visible following prolonged autoradiographic exposure), AIB#314 and the semi-random pool 2 ODNs generated RNase H-mediated cleavage products. In the case of the semi-random pool, two sites of cleavage separated by about 25 bases were identified. Both of these regions contain GUN sites which are complementary to the CA in the ODN. Although semi-random pool 1 did not generate RNase H cleavage products defined by the AIB# set of primers, we have obtained sites from pool 1 on the murine DNA methyl transferase MRNA.

The sequences of the labeled amplified products using the AIB# primer-set were as follows:

For AIB#314

3' CGCCACTGGGCCCTCTAGACTTAA GGGG TTTATA . . . 5' Seq ID 22

From the 3' end, the first 24 nucleotides are from the ligated linker β. The next four G's are from the terminal deoxynucleotidyl transferase reaction. The next segment TTTATA is complementary to nucleotides 327–332 of AIB1 mRNA. The remaining nucleotides (not shown) are complementary to nucleotides 333–558 of AIB1 mRNA.

For AIB#298:

24 nucleotides from linker β plus 3–4 G's from TdT reaction plus complement of nucleotides 297–558 of AIB1 mRNA.

For Semi-random Pool 2

First product: 24 nucleotides from linker β+3–4 G's from the TdT reaction+complement of nucleotides 265–558 of AIB1 MRNA.

Second product: 24 nucleotides from linker β+3–4 G's from the TdT reaction+complement of nucleotides 327–558 of AIB1 MRNA.

The sequences of the labeled amplified products using the A# primer-set were as follows:

For AIB#314: 24 nucleotides from linker β+3–4 G's from the TdT reaction+complement of nucleotides 327–846 of AIB1 mRNA.

For AIB#298: 24 nucleotides from linker β+3–4 G's from the TdT reaction+complement of nucleotides 297–846 of AIB1 mRNA.

For Semi-random Pool 2

First product: 24 nucleotides from linker β+3–4 G's from the TdT reaction+complement of nucleotides 265–846 of AIB1 mRNA.

Second product: 24 nucleotides from linker β+3–4 G's from the TdT reaction+complement of nucleotides 327–846 of AIB1 mRNA.

EXAMPLE 2

This is an example of site mapping using the mRNA encoding murine DNA methyltransferase (Mtase). Three potential sites for testing ODN accessibility were chosen based upon the criteria that each ODN spanned a potential hammerhead ribozyme cleavage site (NUH, where N=A, C, G or U and H=A, C or U) and each of these sites had a different predicted secondary structure based upon the mFOLD of Michael Zuker. The three antisense ODNs (AS351, AS398 and AS498) were all directed to potential binding sites downstream of the AUG translational initiation codon.

The nucleotide sequences listed below were prepared using standard phosphoramidite synthesis chemistry on a commercial DNA/RNA synthesizer. All linkages were phosphodiester.

| Defined ODNs | | |
|---|---|---|
| Sense Control | d(GCAAACAGAAATAAAAAGCCA) | Seq ID 23 |
| Scrambled Control | d(TCGTGCCCACGGGTCATGTTGT) | Seq ID 24 |
| AS351 | d(CCGTTCTCCAAGGACAAATCCTTATT) | Seq ID 25 |
| AS398 | d(TCCCGTTGGCGGGACAACCGTTG) | Seq ID 26 |
| A5498 | d(GGGTGTCACTGTCCGACTTGCT) | Seq ID 27 |

| Primers for MTase gene | | |
|---|---|---|
| Rh-ODNM | d(CTCCTTTGATTTCCGCCTCAATG) | Seq ID 28 |
| ODNM | d(GCAAACAGAAATAAAAAGCCA) | Seq ID 29 |

Primer Rh-ODNM was 5' end-labeled with rhodamine.

| Primers for murine β-actin gene | | |
|---|---|---|
| Fl-ODNβ | d(GAAGCAATGCTGTCACCTTCCC) | Seq ID 30 |
| ODNβ | d(GCGGACTGTTACTGAGCTGCGT) | Seq ID 31 |

Primer FL-ODNβ was 5' end labeled with fluorescein.

In Vitro Transcriptions

For run-off transcriptions, the plasmid Bluescript-MTase containing murine MTase cDNA was linearized with SalI, phenol extracted and ethanol precipitated. Run-off transcription was performed in 100 μl of a mixture containing 50 ng/μl linearized plasmid DNA, 40 mM Tris-HCl, pH 7.9, 10 mM dithiothreitol (DTT), 6 mM $MgCl_2$, 2 mM spermidine, 2 U/μl RNasin, 100 μM rNTPs, 2 μCi/μl [α-$^{32}$P]UTP and 2 U/μl T3 RNA polymerase. After 1 hr incubation at 37° C., 25 U RNase-free DNase I was added and the mixture incubated further for 15 min at 37° C. The transcript was purified on a 6% polyacrylamide gel containing 8M urea, localized by autoradiography and eluted by crushing the gel slices in 0.5 M ammonium acetate, 1 mM EDTA, 0.2% SDS. After subsequent phenol extraction, the transcript was concentrated by ethanol precipitation. The RNA was dissolved in sterile water, quantified and stored at −20° C.

Preparation of Cell Extracts

Polymerase III extracts were prepared as described in Example 1, except that NIH3T3 cells were used instead of MCF-7 cells.

RNase H Digestion $^{32}$P-labeled in vitro transcribed substrate RNA (1 nM), prepared as described above, was incubated with different concentrations of antisense ODN (1.5, 10 and 50 nM; molar ratios 1:1, 1:5, 1:10 and 1:50 substrate:ODN). The reactions were carried out in a volume of 10 μl in 40 mM Tris-HCl, pH 7.5, 4 mM $MgCl_2$, 1 mM DTT, and III polymerase 1 μl extract containing RNase H activity at 37° C. for 1 min. Reactions were stopped with loading buffer and loaded onto a 6% polyacrylamide gel containing 8 M urea. Radioactive bands were analyzed and quantified using a Phosphorimager® (Molecular Dynamics). The RNA transcript (1200 nt) was cleaved by the antisense ODNs, but not by the sense control ODN. The cleavage products were of the expected size, e.g., 960 and 230 nt for AS398 and 860 and 330 nt for AS498. Under the conditions utilized, quantitative analyses of substrate cleavage following electrophoresis in denaturing polyacrylamide gels revealed a reduction of MTase transcript of 90–95% with ODN AS498, 85% with AS398 and 80% with AS351. Experiments using *E. Coli* derived RNase H in place of cellular extract derived RNase H gave nearly identical results.

Mapping with Endogenous MTase mRNA

These RNase H mediated cleavage experiments were carried out in a total volume of 30 μl, containing 20 μl polymerase III extract, 1 mM DTT, 20–40 U RNasin, and 50 nM each of the various antisense ODNS. The ODNs and RNA were incubated for 5–10 min at 37° C. and the mixture was then digested with DNase I for 45 min at 37° C. followed by phenol extraction and ethanol precipitation. Reverse transcription was performed according to the manufacturer's protocol (Life Technologies, Grand Island, N.Y.) using 50 ng random hexamer primer and 10 U M-MLV-RT. An aliquot (18 μl) of the RT reaction was amplified using the MTase primers Rh-ODNM and ODNM, and the remaining aliquot (2 μl) was amplified using the β-actin primers Fl-ODNβ and ODNβ for 1 min at 94° C., 1 min at 50° C. and 2 min at 72° C., for 25–28 cycles in a volume of 50 μl. The product from RT-PCR amplification of the MTase mRNA is 610 bp in length. β-actin MRNA, which is abundant in these extracts, served as an internal standard as well as loading control. The product from RT-PCR amplification of the β-actin mRNA is 445 bp in length. Reaction products were analyzed and quantified on an Applied Biosciences Prism® 377 DNA Sequencer using ABL Genescan® analysis software v.2.1. For a size marker, the Genescan-2500 TAMARA standard (ABI) with molecular lengths (bp) 827, 536, 490, 470, 361, 286, 269, 238, 233, 222, 186, 172, 116, 109, 94 and 37 was utilized.

The experiment using the sense control ODN showed the expected products of 610 bp for MTase mRNA and 445 bp for β-actin mRNA. In contrast treatment of the cell extract with antisense ODNs resulted in a significant reduction in the MTase mRNA signal without reduction in the β-actin mRNA signal. Genescan analysis of the electrophoresed PCR products revealed reductions in MTase mRNA of about 85% with AS498, 58% with AS398 and 20% with AS351.

All publications cited in this application are incorporated herein by reference.

What is claimed is:

1. A method for identifying sites on a target RNA which are accessible to pairing by antisense DNA, ribozymes or DNAzymes which comprises:
   a) incubating native or in vitro-synthesized target RNA with a random or semi-random ODN library and RNase H, or with a semi-random ribozyme or DNAzyme library, under hybridization conditions in a reaction medium which is a cell extract containing endogenous RNA-binding proteins, or which mimics a cell extract due to presence of one or more RNA-binding proteins, whereby any antisense ODN, ribozyme or DNAzyme within the library which is complementary to an accessible site in the target RNA hybridizes to that site and the RNA is cleaved at that site;
   b) annealing to the target RNA an ODN primer P1 which is complementary to a region of the target RNA downstream from the portion of the target RNA molecule under study, and incubating the primed target RNA with a reverse transcriptase and dNTPs, whereby the RNA is copied into DNA from the 3' end of P1 to the site of cleavage created by the antisense ODN/RNase H, ribozyme or DNAzyme, creating a first strand DNA molecule with a 3' end that is complementary to the 5' end of the target RNA at the cleavage site;
   c) incubating the first strand DNA with guanosine triphosphate in presence of terminal deoxynucleotidyl transferase to add an $(rG)_{2-4}$ tail on the 3' end of the DNA molecule;
   d) incubating the 3'-tailed DNA in the presence of a DNA ligase with a double-stranded ODN linker having a $3'C_{2-4}$ overhang on one strand, whereby the tail base pairs with the overhang and the other strand is ligated to the 3'-tailed DNA;
   e) mixing the ligated DNA with an ODN linker primer LP which is complementary to the strand of the linker which is ligated to the $(rG)_n$ tail and with a primer P2 which is complementary to the original target RNA in a region which corresponds to or is at least partially upstream from the region which is bound by P1, but it is downstream of the portion of the target RNA which is under study, and carrying out PCR in presence of a DNA polymerase and dNTPs to amplify DNA segments defined by primers LP and P2; and
   f) sequencing the PCR-amplified DNA to determine the cleavage site on the target RNA.

2. The method of claim 1 wherein in step (a) a random or semi-random ODN, ribozyme or DNAzyme library is incubated in cell extract containing endogenous target mRNA, endogenous RNA-binding proteins and endogenous RNase H.

3. The method of claim 2 wherein the library is a semi-random library of ODNs containing fixed nucleotides directed to potential hammerhead ribozyme cleavage sites in the target mRNA.

4. The method of claim 1 wherein the target RNA is an in vitro-synthesized RNA and the reaction medium in step (a)

mimics a cell extract due to presence of one or more RNA-binding proteins selected from the group consisting of heterogeneous nuclear RNA-binding proteins and messenger RNA-binding proteins.

5. The method of claim 4 wherein a semi-random library of ODNs containing fixed nucleotides directed to potential hammerhead ribozyme cleavage sites in the target mRNA is used in step (a).

6. The method of claim 4 wherein the medium contains heterogeneous nuclear ribonucleoprotein A1.

7. A method for identifying sites on a target RNA which are accessible to pairing by antisense DNA, ribozymes or DNAzymes, which comprises
   a) incubating native or in vitro-synthesized target RNA with a random or semi-random ODN library and RNase H, or with a semi-random ribozyme or DNAzyme library, under hybridization conditions in a reaction medium which is a cell extract containing endogenous RNA-binding proteins, or which mimics a cell extract due to presence of one or more RNA-binding proteins, whereby any antisense ODN, ribozyme or DNAzyme within the library which is complementary to an accessible site in the target RNA hybridizes to that site and the RNA is cleaved at that site; and
   b) determining the location of the cleavage site.

8. The method of claim 7 wherein in step (a) a random or semi-random ODN, ribozyme or DNAzyme library is incubated in cell extract containing endogenous target mRNA, endogenous RNA-binding proteins and endogenous RNase H.

9. The method of claim 8 wherein the library is a semi-random library of ODNs containing fixed nucleotides directed to potential hammerhead ribozyme cleavage sites in the target mRNA.

10. The method of claim 7 wherein the target RNA is an in vitro-synthesized RNA and the reaction medium in step (a) mimics a cell extract due to presence of one or more RNA-binding proteins selected from the group consisting of heterogeneous nuclear RNA-binding proteins and messenger RNA-binding proteins.

11. The method of claim 10 wherein a semi-random library of ODNs containing fixed nucleotides directed to potential hammerhead ribozyme cleavage sites in the target mRNA is used in step (a).

12. The method of claim 10 wherein the medium contains heterogeneous nuclear ribonucleoprotein A1.

13. The method of claim 1 wherein P1 is labeled with one member of a specific binding pair.

14. The method of claim 13 wherein said first strand cDNA is affinity purified using a second member of said specific binding pair.

15. The method of claim 13 wherein said specific binding pair comprises biotin.

16. The method of claim 1 wherein said primer LP or P2 is labeled with one member of a specific binding pair.

17. The method of claim 16 wherein said PCR-amplified DNA is affinity purified using a second member of said specific binding pair.

18. The method of claim 17 wherein said specific binding pair comprises biotin.

* * * * *

UNITED STATES PATENT AND TRADEMARK OFFICE
CERTIFICATE OF CORRECTION

PATENT NO. : 6,562,570 B1
DATED : May 13, 2004
INVENTOR(S) : John J. Rossi et al.

It is certified that error appears in the above-identified patent and that said Letters Patent is hereby corrected as shown below:

Column 7,
Line 34, "sperate" should read -- separate --;

Column 9,
Line 36, delete second occurrence of "the" before "M-MLV";
Line 37, "95" should be -- 95°C --;

Column 10,
Lines 36 and 37, delete "Lane 8-RT-TDPCR product from MCF-7 cell extract treated with control ODN (SEQ ID 1)";
Lines 38 and 39, delete "(band is not visible in this exposure, but it is visible following prolonged autoradiographic exposure)"
Lines 59, 62, and 66, "558" should be -- 546 --;

Column 11,
Line 2, "558" should be -- 546 --
Lines 7, 10, 14 and 17, "846" should be -- 830 --;
Line 46, (in the table), "A5498" should be -- AS498 --.

Column 12,
Line 25, "III polymerase 1µ1" should be -- 1µ1 polymerase III --.

Signed and Sealed this

Twenty-eighth Day of September, 2004

JON W. DUDAS
*Director of the United States Patent and Trademark Office*

SEQUENCE LISTING

```
<160> NUMBER OF SEQ ID NOS: 31

<210> SEQ ID NO 1
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: Non-sense control--Example 1

<400> SEQUENCE: 1
ccgtatcgct cgggttaagc                                            20

<210> SEQ ID NO 2
<211> LENGTH: 20
<212> TYPE: DNA
<213> ORGANISM: Homo sapiens

<400> SEQUENCE: 2
tattggtctc tgagtccacc                                            20

<210> SEQ ID NO 3
<211> LENGTH: 20
<212> TYPE: DNA
<213> ORGANISM: Homo sapiens

<400> SEQUENCE: 3
ctgcaggtaa gaccttgtcc                                            20

<210> SEQ ID NO 4
<211> LENGTH: 20
<212> TYPE: DNA
<213> ORGANISM: Homo sapiens

<400> SEQUENCE: 4
ctcccgtctc cgtttttgac                                            20

<210> SEQ ID NO 5
<211> LENGTH: 20
<212> TYPE: DNA
<213> ORGANISM: Homo sapiens

<400> SEQUENCE: 5
tatatttact ttcctgctcc                                            20

<210> SEQ ID NO 6
<211> LENGTH: 20
<212> TYPE: DNA
<213> ORGANISM: Homo sapiens

<400> SEQUENCE: 6
catccaatgc ctgaagtaaa                                            20

<210> SEQ ID NO 7
<211> LENGTH: 24
<212> TYPE: DNA
```

```
<213> ORGANISM: Homo sapiens

<400> SEQUENCE: 7
cctgaagtaa aagcggtcct aagg                                          24

<210> SEQ ID NO 8
<211> LENGTH: 30
<212> TYPE: DNA
<213> ORGANISM: Homo sapiens

<400> SEQUENCE: 8
gcggtcctaa ggagtctttta tcaataactc                                   30

<210> SEQ ID NO 9
<211> LENGTH: 19
<212> TYPE: DNA
<213> ORGANISM: Homo sapiens

<400> SEQUENCE: 9
ctctggcgaa tttcaggac                                                19

<210> SEQ ID NO 10
<211> LENGTH: 22
<212> TYPE: DNA
<213> ORGANISM: Homo sapiens

<400> SEQUENCE: 10
caggactggc gtttatgtct tc                                            22

<210> SEQ ID NO 11
<211> LENGTH: 28
<212> TYPE: DNA
<213> ORGANISM: Homo sapiens

<400> SEQUENCE: 11
gtcttccaga atatcatgtg gtgttttc                                      28

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Ligation
      linker upper strand

<400> SEQUENCE: 12
gcggtgaccc gggagatctg aattccc                                       27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Ligation
      linker lower strand

<400> SEQUENCE: 13
aattcagatc tcccgggtca ccgc                                          24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Linker
```

```
                        primer

<400> SEQUENCE: 14
gcggtgaccc gggagatctg aattc                                           25

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence:  Ribozyme
      core

<400> SEQUENCE: 15
cugaugaguc cgugaggacg aaa                                             23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:  Chimeric
      ribozyme core

<400> SEQUENCE: 16
cugaugagag gagtgcctcg aaa                                             23

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence:  Ribozyme
      core

<400> SEQUENCE: 17
cugauggucc guaggacgaa ac                                              22

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence:  DNAzyme
      core

<400> SEQUENCE: 18
tccgagccgg acga                                                       14

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:  DNAzyme
      core

<400> SEQUENCE: 19
aggctagcta caacga                                                     16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence:  DNAzyme
      core
```

<400> SEQUENCE: 20
gggctagcta caacga                                                   16

<210> SEQ ID NO 21
<211> LENGTH: 30
<212> TYPE: RNA
<213> ORGANISM: Artificial Sequence
<220> FEATURE:
<223> OTHER INFORMATION: Description of Artificial Sequence: Hairpin
      ribozyme sequence

<400> SEQUENCE: 21
accaggaaac cacguuguau auuaccuggu                                    30

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Linker
      plus AIB1 segment amplification product

<400> SEQUENCE: 22
cgccactggg ccctctagac ttaaggggtt tata                               34

<210> SEQ ID NO 23
<211> LENGTH: 21
<212> TYPE: DNA
<213> ORGANISM: murine

<400> SEQUENCE: 23
gcaaacagaa ataaaaagcc a                                             21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Scrambled
      control-Example 2

<400> SEQUENCE: 24
tcgtgcccac gggtcatgtt gt                                            22

<210> SEQ ID NO 25
<211> LENGTH: 26
<212> TYPE: DNA
<213> ORGANISM: murine

<400> SEQUENCE: 25
ccgttctcca aggacaaatc cttatt                                        26

<210> SEQ ID NO 26
<211> LENGTH: 23
<212> TYPE: DNA
<213> ORGANISM: murine

<400> SEQUENCE: 26
tcccgttggc gggacaaccg ttg                                           23

<210> SEQ ID NO 27
<211> LENGTH: 22
<212> TYPE: DNA
<213> ORGANISM: murine

```
<400> SEQUENCE: 27
gggtgtcact gtccgacttg ct                                        22

<210> SEQ ID NO 28
<211> LENGTH: 23
<212> TYPE: DNA
<213> ORGANISM: murine

<400> SEQUENCE: 28
ctcctttgat ttccgcctca atg                                       23

<210> SEQ ID NO 29
<211> LENGTH: 21
<212> TYPE: DNA
<213> ORGANISM: murine

<400> SEQUENCE: 29
gcaaacagaa ataaaaagcc a                                         21

<210> SEQ ID NO 30
<211> LENGTH: 22
<212> TYPE: DNA
<213> ORGANISM: murine

<400> SEQUENCE: 30
gaagcaatgc tgtcaccttc cc                                        22

<210> SEQ ID NO 31
<211> LENGTH: 22
<212> TYPE: DNA
<213> ORGANISM: murine

<400> SEQUENCE: 31
gcggactgtt actgagctgc gt                                        22
```